(12) United States Patent  
Li et al.

(10) Patent No.: US 9,080,202 B2  
(45) Date of Patent: Jul. 14, 2015

(54) METHOD OF SNP DETECTION BY USING GENE DETECTION TECHNIQUE IN BEAD-BASED MICROFLUIDICS

(71) Applicant: National Taiwan University, Taipei (TW)

(72) Inventors: Kan-Chien Li, Taipei (TW); Shih-Torng Ding, Taipei (TW); En-Chung Lin, Taipei (TW); Yen-Wen Lu, Taipei (TW)

(73) Assignee: NATIONAL TAIWAN UNIVERSITY, Taipei (TW)

( * ) Notice: Subject to any disclaimer, the term of this patent is extended or adjusted under 35 U.S.C. 154(b) by 0 days.

(21) Appl. No.: 14/157,781

(22) Filed: Jan. 17, 2014

(65) Prior Publication Data

US 2015/0125855 A1     May 7, 2015

(30) Foreign Application Priority Data

Nov. 6, 2013   (TW) .............................. 102140240 A

(51) Int. Cl.  
*C12Q 1/68* (2006.01)

(52) U.S. Cl.  
CPC .................................... *C12Q 1/6827* (2013.01)

(58) Field of Classification Search  
None  
See application file for complete search history.

(56) References Cited

U.S. PATENT DOCUMENTS

| 2009/0112481 A1* | 4/2009 | Cao .................................. 702/19 |
| 2010/0133118 A1* | 6/2010 | Sosnowski et al. ......... 205/777.5 |
| 2012/0116687 A1* | 5/2012 | Kanderian ....................... 702/20 |

* cited by examiner

*Primary Examiner* — James Martinell  
(74) *Attorney, Agent, or Firm* — Birch, Stewart, Kolasch & Birch, LLP

(57) ABSTRACT

The present invention provides a method of SNP detection by using gene detection in bead-based microfluidics comprising following steps: (a) preparing a microbead with a duplex DNA; (b) inserting a dye into the duplex DNA; (c) delivering the microbead into a microchannel with a temperature gradient region; (d) heating the temperature gradient region to denature the duplex DNA; (e) monitoring a fluorescence intensity of the duplex DNA during the step (d) to obtain a melting curve; and (f) determining the SNP by a melting curve analysis method; wherein the duplex DNA is synthesized by a target single-strand DNA and an allele-specific probe. Furthermore, the present invention offers a temperature gradient region to enhance the measurement accuracy. The continuous-flow mechanism in this region is validated and optimized.

12 Claims, 7 Drawing Sheets  
(6 of 7 Drawing Sheet(s) Filed in Color)

METHOD OF SNP DETECTION BY USING GENE DETECTION TECHNIQUE IN BEAD-BASED MICROFLUIDICS

BACKGROUND OF THE INVENTION

1. Field of the Invention

The present invention relates to a method of SNP (Single-nucleotide polymorphism) detection by using gene detection technique. More particularly, the present invention relates to a method of SNP detection by using gene detection technique in bead-based microfluidics with a well-controlled temperature-gradient region inside the microchannels.

2. Description of Related Art

Single nucleotide polymorphisms (SNPs) are one of the most common types in genetic variations, estimated to occur at 1 out of every 1,000 bases in the human genome, which means more than 10 million points of SNPs occurring across the human genome. SNPs are important markers that link sequence variations to phenotypic changes; such researches are expected to advance the understanding of human physiology and to elucidate the molecular bases of diseases. To date, a great deal of work has been devoted to developing accurate, rapid, and cost-effective technologies for SNP genotyping. The genotyping procedures typically involve the amplification of allele-specific products for SNP of interest, followed by the genotype detection techniques, such as enzymatic ligation, enzymatic cleavage, primer extension, split DNA enzymes G-quadruplex, sequencing, pyrosequencing, and mass spectroscopy. All of these techniques utilize enzymes, molecular beacon, or fluorescent dyes to label the DNA probes, leading to the requirement of high reagent cost or complicate procedures.

On the other hand, the dynamic allele-specific hybridization (DASH) technique has drawn great attention in SNP genotyping since it doesn't require the complex and expensive modification procedures on enzymes or fluorescent molecules. A conventional DASH procedure is described as follows. A target sequence is amplified by PCR in which one primer is biotinylated. The biotinylated product strand is bound to a streptavidin-coated microtiter plate well, and the non-biotinylated strand is rinsed away with alkali. An oligonucleotide probe, specific for one allele, is hybridized to the target at low temperature. This forms a duplex DNA region that interacts with a double strand-specific intercalating dye. Upon excitation, the dye emits fluorescence proportional to the amount of double stranded DNA (probe-target duplex) present. The sample is then steadily heated while fluorescence is continually monitored. A rapid fall in fluorescence indicates the denaturing (or "melting") temperature of the probe-target duplex. When performed under appropriate buffer and dye conditions, a single-base mismatch between the probe and the target results in a dramatic lowering of melting temperature ($T_m$) that can be easily detected.

Furthermore, miniaturized devices, for instance microfluidic or lab-on-a-chip devices, have brought many advantages over their analogues at the macroscale, including portability, reduced sample consumption, rapid reaction times, and high throughput. The microbeads can serve as a vehicle to immobilize the target biomolecules, carry the biomolecules for a series of reactions. Bead-based microfluidic devices thus can significantly simplified the tedious and labor-intensive washing procedures of traditional DNA/RNA purification and double-stranded DNA isolation process.

In recent years, the development in microfluidics further promotes melting analysis within the aforesaid miniature device, which not only can reduce the reagent cost but also provide the possibility point-of-care molecular diagnosis. The DNA melting analysis in microfluidic device usually resorts to solid or liquid phase on sample preparations, in which either DNA immobilization on channel surfaces is required or only single analysis is allowed. However, some related arts, such as Russom et al, "rapid melting curve analysis on monolayered beads for high-throughput genotyping of single-nucleotide polymorphisms" (Anal. Chem. 78, 2006 3515867), provide a rapid solid-phase melting curve analysis method for single-nucleotide polymorphism (SNP) genotyping. The melting curve analysis was based on dynamic allele-specific hybridization (DASH). The DNA duplexes were conjugated on beads that are immobilized on the surface of a microheater chip with integrated heaters and temperature sensors, and a melting curve was obtained. However, those related arts failed to teach the temperature gradient region enhancing the measurement sensitivity and accuracy. To address these limitations, a bead-based melting analysis with temperature gradient configuration is required.

SUMMARY OF THE INVENTION

A primary objective of the present invention is to provide a method of SNP detection by using gene detection technique in bead-based microfluidics. The present invention is designed to use special microbeads as a mobile support to immobilize target DNA molecules flowing through a well-controlled temperature-gradient region inside microchannels for melting analysis.

To achieve the foregoing objective, the present invention provides a method of SNP detection by using gene detection in bead-based microfluidics comprising following steps: (a) preparing a microbead with a duplex DNA; (b) inserting a dye into the duplex DNA; (c) delivering the microbead into a microchannel with a temperature gradient region; (d) heating the temperature gradient region to denature the duplex DNA; (e) monitoring a fluorescence intensity of the duplex DNA during the step (d) to obtain a melting curve; (f) determining the SNP by a melting curve analysis method; wherein the duplex DNA is synthesized by a target single-strand DNA and an allele-specific probe.

Preferably, the target single-strand DNA may be amplified by PCR before the step (a).

Preferably, after the target single-strand DNA may be amplified by PCR, the target single-strand DNA may be biotinlayted and the microbead may be coated with streptavidin. In addition, the target single-strand DNA may be immobilized onto the microbead by a biotin-streptavidin interaction.

Preferably, after the target single-strand DNA may be immobilized onto the microbead, the allele-specific probe may be hybridized with the target single-strand DNA.

In a preferred embodiment of the present invention, a patterned glass configured with a thermometer and a heater may be bonded onto the microchannel; wherein a temperature of the temperature gradient region is controlled by a heater, and a temperature of the temperature gradient region is detected by the thermometer.

In a preferred embodiment of the present invention, the fluorescence intensity may be monitored by a CCD camera.

In a preferred embodiment of the present invention, the dye may be an intercalating dye.

Preferably, the intercalating dye may comprise SYBR Green I, EtBr or EVE Green.

In a preferred embodiment of the present invention, the temperature gradient region is heated ranged from 50° C. to 95° C., preferably, from 65° C. to 85° C.

This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

Many of the attendant features and advantages of the present invention will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where.

DESCRIPTION

Figure 1:
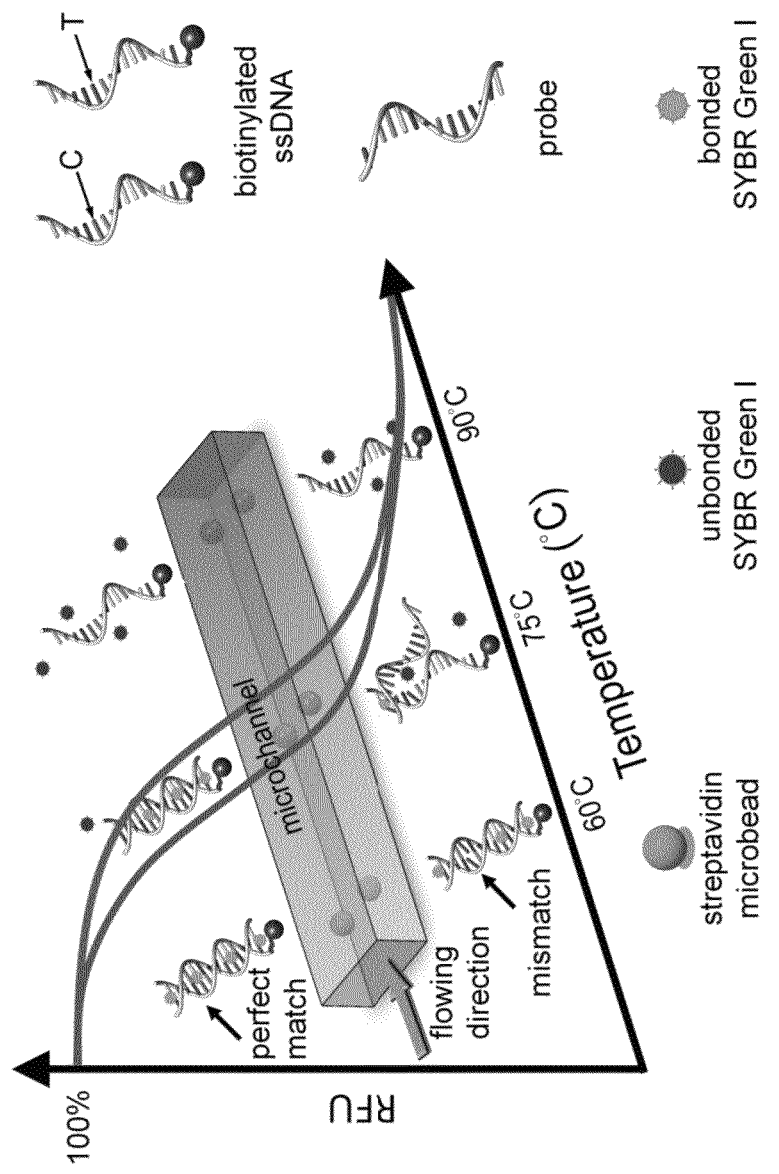
FIG. 1 is a schematic flowchart of melting analysis bead-based microfluidic device for SNP genotyping.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless defined otherwise, all technical and scientific terms used herein have the same meaning as commonly understood by one of the ordinary skill in the art to which this invention belongs.

Various embodiments will now be described more fully with reference to the accompanying drawings, in which illustrative embodiments are shown. The inventive concept, however, may be embodied in various different forms, and should not be construed as being limited only to the illustrated embodiments. Rather, these embodiments are provided as examples, to convey the inventive concept to one skilled in the art. Accordingly, known processes, elements, and techniques are not described with respect to some of the embodiments.

The singular forms "a", "and", and "the" are used herein to include plural referents unless the context clearly dictates otherwise.

In the present invention, a genotyping system was established by integrating the DASH technique with a bead-based microfluidic device. The present invention not only preserved the flexible and accurate SNP detection scheme from the gene detection, but it also possessed the advantage of having a minimal amount of the reagents. The microbeads flowed into the microfluidic device, thereby immobilizing the target DNA into designed microfluidics with continuous flow, with the Melting Curve analysis then being conducted. Genotyping for both synthetic DNA and genomic DNA from Landrace sows on a SNP—ataxia-telangiectasia-mutated (ATM) gene—were discriminated via Melting Curve analysis. As the ATM gene in Landrace sows was recently found to play important roles in total number of piglets born, number born alive and average birth weight due to its differential expression between the morula and blastocyst stages, the present invention exhibited this bead-based SNP detection system with great potential being an effective approach to select useful biomarkers and to improve the reproductive traits in pigs.

To achieve the desired effect, the present invention offers a method of SNP detection by using gene detection in bead-based microfluidics comprising following steps: (a) preparing a microbead with a duplex DNA; (b) inserting a dye into the duplex DNA; (c) delivering the microbead into a microchannel with a temperature gradient region; (d) heating the temperature gradient region to denature the duplex DNA; (e) monitoring a fluorescence intensity of the duplex DNA during the step (d) to obtain a melting curve; and; (f) determining the SNP by a melting curve analysis method; wherein the duplex DNA is synthesized by a target single-strand DNA and an allele-specific probe.

Before the step (a), the target single-strand DNA may be amplified by PCR. Furthermore, after the target single-strand DNA may be amplified by PCR, the target single-strand DNA may be biotinlayted and the microbead may be coated with streptavidin. Then, the target single-strand DNA may be immobilized onto the microbead by a biotin-streptavidin interaction.

Wherein, after the target single-strand DNA may be immobilized onto the microbead, the allele-specific probe may be hybridized with the target single-strand DNA.

In a preferred embodiment of the present invention, a patterned glass configured with a thermometer and a heater may be bonded onto the microchannel; wherein a temperature of the temperature gradient region is controlled by a heater and a temperature of the temperature gradient region is detected by the thermometer.

In a preferred embodiment of the present invention, the fluorescence intensity may be monitored by a CCD camera.

In a preferred embodiment of the present invention, the dye may be an intercalating dye.

Preferably, the intercalating dye may comprise SYBR Green I, EtBr or EVE Green.

In a preferred embodiment of the present invention, the temperature gradient region is heated ranged from 50° C. to 95° C.; preferably from 65° C. to 85° C.

The following descriptions are provided to elucidate certain aspects of the present invention and to aid those of skilled in the art in practicing this invention. These Examples are merely exemplary embodiments and in no way to be considered to limit the scope of the invention in any manner.

Design and Working Principle

Dynamic Allele-Specific Hybridization Method

In dynamic allele-specific hybridization (DASH) method of the present invention, an oligonucleotide probe, specific for one allele, is hybridized to the target. This forms a duplex DNA region that interacts with a double-stranded DNA (dsDNA) specific intercalating dye. Upon excitation, the dye emits fluorescence proportional to the amount of dsDNA. Therefore, when the sample is steadily heated, the dsDNA begins to denature and the amount of dsDNA decreases, leading to the decrease of the fluorescent intensity. When the temperature is close to the melting temperature ($T_m$) of the probe-target duplex, the fluorescence intensity falls rapidly. An allele specific probe, which can form perfect dsDNA with wildtype single-stranded DNA (ssDNA) and one base pair mismatched with ssDNA containing SNP, is designed to separate the melting temperatures during the melting curve analysis. The present invention adopts this method and further conjugates the DNA sequences on microbeads to reduce the reagent use.

Bead-Based Microfluidic Device for SNP Detection

FIG. 1 illustrates the melting analysis with a continuous-flow bead-based microfluidic device for SNP genotyping, and the steps are described as follows: (a) the duplex detection sample immobilized onto a microbead was loaded into the temperature gradient region inside a microchannel and the fluorescent intensity was real-time detected; and (b) melting curve analysis of perfect-match sample and mismatch sample was conducted and obtained. When the microbeads with DNA duplex gradually pass through the temperature gradient (65° C. to 85° C.), the DNA duplex denature and the intercalated fluorescent dyes are released, inducing the fluorescent signals to decay.

In particular, Silica microbeads of 20 μm in diameter are coated with streptavidin and employed to bind with the biotinylated ssDNA. The DNA probe and intercalating dye are sequentially added to form the dye-intercalated probe-target conformation. After conjugated with the target-probe duplex, the microbeads are delivered into microchannels. The melting curve analysis is then conducted to in situ monitor the samples as the temperature increases during the DNA denaturation for the DASH technique. Due to the nucleotide mutation, one base mismatch between the target-probe duplex causes a lower $T_m$ than the perfect match one; the SNP thus can be detected.

Temperature Gradient Region of Bead-Based Microfluidic

Figure 2:
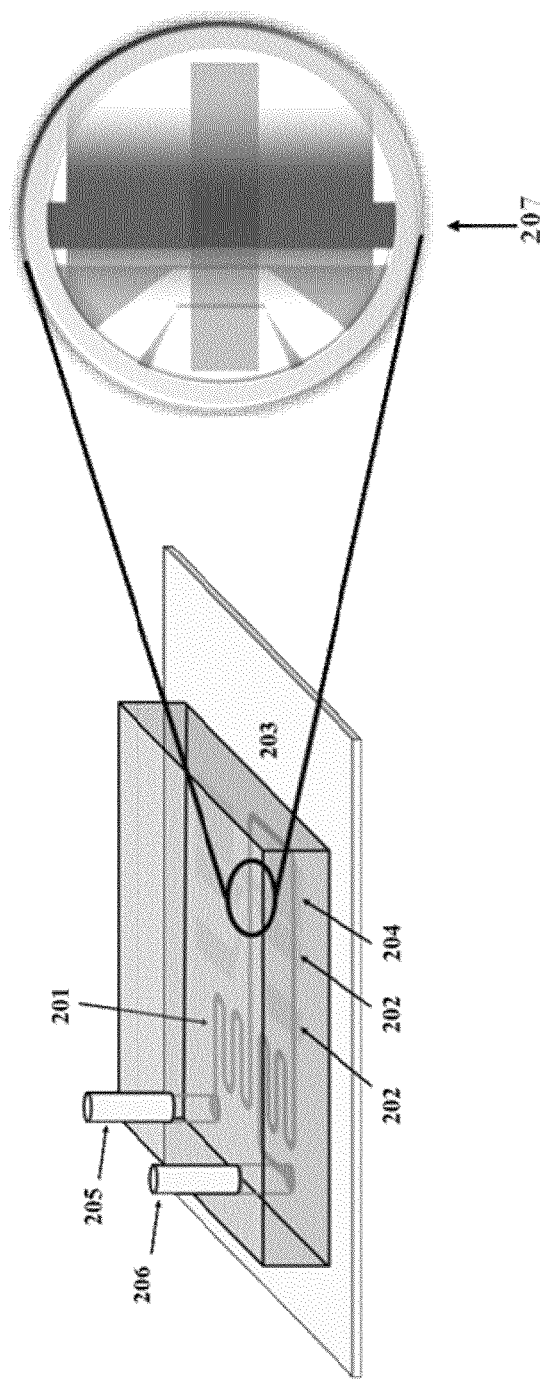
FIG. 2 is a three-dimensional diagram for SNP detection chip with ITO patterned glass.

The microfluidic device consisted of an ITO glass was bonded onto a polydimethylsiloxane (PDMS) slab with microchannels. Before bonding, the ITO glass was patterned to define heaters and temperature sensors (i.e. thermometer), as shown in FIG. 2. The temperature sensors were calibrated using mictoIR camera and thermocouple. Referring to FIG. 2, when the microbeads flow inside the microchannel 201, the microbeads with DNA duplex would flow through a temperature gradient region 207 onto which an ITO patterned glass 203 bonded. Wherein, the heater 204 was established at the right side of ITO glass 203, and the heat generated from the heater 204 would diffuse from higher temperature region (right side of ITO glass 203) to lower temperature region (left side of ITO glass 203). Then, the temperature gradient region 207 was formed, and the thermometers 202 were responsible for detecting the temperature of temperature gradient region 207. Fluid velocity field simulation was conducted by using the commercial finite element analysis software, COMSOL Multiphysics Version 4.0a (COMSOL, Inc., Burlington, Mass., USA). The model was based on the steady-state Nervier-Stokes' for an incompressible fluid. The parameters used in the simulation are as follows: 1000 kg/m³ for density, 1 mPa·s for dynamic viscosity. A uniform velocity of 0.01 m s$^{-1}$ was applied at the inlet 205 and a zero pressure boundary condition was applied at the outlet 206. No slip boundary conditions were set for the channel wells. The simulation result supported the hypothesis of the present invention that the flow velocity would increase at the outlet and cause a lower pressure to attract the microbeads.

The method of defining the thermometers or heaters onto ITO glass comprises, but not limited thereto, etching, masking, and the like. Any changes and modifications which fall within the true scope of the invention, as defined in the appended claim, occurring to those skilled in the art.

Material and Methods

A method of SNP detection by using gene detection in bead-based microfluidics disclosed by the present invention will be described in further detail with reference to several aspects and examples below, which are not intended to limit the scope of the present invention.

Microbead and Functionalization

Plain 20 μm polystyrene microbeads (Cat. 18329-5, Polysciences Inc., Warrington, Pa., USA) at 700 beads μL$^{-1}$ were not merely used to provide a relatively high surface-to-volume ratio, but also enhanced reaction kinetics for better sensitivity and larger mutation discrimination. For SNP detection, streptavidin-coated 20 μm diameter silica microbeads (Cat. 141048-05, Corpuscular Inc., Coldspring, N.Y., USA) at 250 beads μL$^{-1}$ were used to form the biological linker between the target sequence and microbeads (biotin-streptavidin). In particular, the microbeads used in the present invention had 30000 parts surface area exposed per unit volume. It means that 30000 parts surface area per unit volume are exposed to environment, and the microbeads has excellent ability for heat transfer to make the heat exchange promptly between the microbeads and environment during heating, so as to ensure that the reaction temperature for DNA duplex on microbeads is the same as the environment temperature.

SNPs Detection Chip and Microchannel Design

The scheme of the chip was shown in FIG. 2. It consisted of a top PDMS layer with microchannels 201 and a bottom ITO glass layer 203 with heaters 204 and thermometers 202. Depending on the vision field of the fluorescence detection system, the distance of these two thermometers 202 were deliberately designed to be 1250 μm. In order to precisely measure and control the temperature, the thermometers 202 were designed and embedded on the chip and closed to the channels. The transparent material of ITO was employed as the thermometer 202 and heater 204. According to the microchannel morphology, the shape of the ITO pattern was designed for sensing the temperature and providing energy to the microchannel for melting curve genotyping.

According to the bead-based microfluidic SNPs detection process, the microbeads should flow with a slow and a stable velocity. With the liquid flowing fast in the microchannel, the temperature field shift, and the fast-flowing microbeads difficult to clearly imaged by a CCD camera with a common exposure time.

The microchannel layout in FIG. 2 was based on the design concerns discussed earlier. A 2-cm long microchannel was designed for the high inner pressure and more stable fluidic field when the liquid filled the microchannels. The width of microchannel was 300 μm to control the flow velocity below 10 μm/second with a micro-syringe and a high precision syringe pump (pump rate=1 μL/hr). The height of the microchannel was 30 μm to ensure only one microbead flowing through at a time. To accommodate the microchannel within a limit space, the microchannel was designed by a serpentine geometry. In addition, since the streptavidin-coated silica microbeads used in the present invention was 20 μm in diameter, the height and width of microchannel were designed at 30 μm and 300 μm respectively.

Heater and Thermometer Design

To generate the desired temperature gradient across detection region, a temperature field was generated by an ITO heater. By controlling the current passing through the heater, the temperature field can be adjusted. The relationship between the current, voltage, and resistance was:

$$P = IV = I^2R = \frac{V^2}{R} \quad (1)$$

where P (Joule/second) is the power, I (Amp) is the current, V (volt) is the voltage, R (ohm) is the resistance.

As the resistance of the material varies at different temperature, the relationship between the resistance (R) and temperature (T) is:

$$R(T) = R_{T_0}[1 + \alpha(T - T_0)] \quad (2)$$

where $T_0$ is the initial temperature and $\alpha$ is the temperature coefficient. The temperature coefficient of the ITO could be calibrated by re-arranging Equation (3.2) as:

$$T = \frac{1}{\alpha}\left(\frac{R}{R_{T_0}} - 1\right) + T_0 \quad (3)$$

Temperature Measurement

To examine the uniformity of the temperature gradient across the entire chip, an infrared camera (TVS-500EX, NEC, Inc.) was used to capture the thermal images. A DC voltage was applied to the heater. Approximately 5 minutes was allowed for the system to become stable so the heat transfer could reach steady. The direction of heat transfer, mostly in the form of heat conduction, was perpendicular to the heater, as shown in the insert of FIG. 2. The insert is a top view of the SNP detection chip, and showed the close-up view of the region of the heater and thermometers for melting curve analysis. The temperature around the heater was the highest and decreased toward both sides of the chip. The temperature gradient thus occurred in the direction parallel to the microchannels.

Once the thermal gradient became stabilized, the measurement from the infrared camera and digital thermometer (DE-3003, DER EE Electrical Instrument, Inc.) were compared. As the temperature on the ITO glass surface could be measured by using a digital thermometer, the temperature of the microchannel ($T_c$) could be derived from Fourier's law of conduction equation:

$$Q = KA\frac{(T_s - T_c)}{\Delta X} \quad (4)$$

where Q is the thermal conduction, $\Delta X$ is distance from the ITO glass surface to the microchannel, K is the thermal conductivity of the PDMS (typical value of $K_{PDMS}$=0.15 W/m), $T_s$ is the temperature of the ITO glass measured from digital thermometer.

DNA Extraction, Amplification and SNP Discovery

The SNP discrimination point ATM-A lying on protein gene (Basic Local Alignment Search Tool: AY587061.1), which has proven to be a possible bio-marker associated with reproductive performance in Landrace sows, was chosen to demonstrate the validity and potential of our SNP detection system. For SNP discovery within the ATM gene, the total of three Landrace sows in Taiwan was used genomic DNA isolated from blood samples obtained from the anterior vena cava using a Puregene™ DNA Purification Kit based on the manufacturer's recommendations (Gentra System, Inc., MN, USA). The primer pairs for the ATM gene were designing by using a porcine nucleotide database (GenBank: AY587061). The translation start site of the ATM gene was present within the exon 3[30]. To amplify the 5'-flanking region (upstream promoter and exon 1 to intron 2 region) sequence of the ATM gene by PCR, the primers were used, as listed in Table 1, led to the amplification of a 1,581-bp fragment. The purified PCR products were directly sequenced with these primers using an automated sequencer (ABI PRISM 3730 DNA Analyzer, Applied 50 Biosystems, Foster City, Calif., USA). The nucleotide sequences were aligned for the detection of SNPs using the program Lasergene (DNAstar, Madison, Wis., USA). For regulatory SNPs, binding motifs of transcription factors in the DNA fragments were estimated using MatInspector software (Genomatix, Munich, Germany).

PCR Preparation

Two steps of PCR procedures, including symmetric PCR and asymmetric PCR, were performed to allow the target ssDNA with proper modifications to bind onto the microbeads. In the symmetric PCR process, genomic DNA was amplified to supply dsDNA containing target SNP point (ATM-A). In the asymmetric PCR process, the products from the first PCR were used as template, and the biotinlayted forward primers were applied to amplify target ssDNA. Moreover, in order to separate the dsDNA template and ssDNA target via agarose gel electrophoresis, primers were designed to produce different length of DNA sequences in each step, which were 91 bp and 73 mer, respectively. Meanwhile, the PCR conditions meanwhile were optimized to ensure sufficient and correct ssDNA were produced, after a series of tests on different concentrations of forward and reverse primers and the annealing temperature in both PCR steeps. The optimized PCR conditions are: 5 ng $\mu L^{-1}$ of genomic DNA, 200 μM dNTP mixture, 0.5 μM of Betaine, 1% of DMSO, 2.5 U Tag in a total reaction volume of 50 μL for the symmetric PCR. In addition, 0.2 μM of forward and reverse primers were used for the symmetric PCR to amplify the target genome region, and 0.5 μM of biotinlayted forward primer were used for the asymmetric PCR to amplify the single-strand DNA containing the ATM-A SNP point. The condition for the symmetric PCR: 94° C. for 5 min followed by 30 cycles of 94° C. for 20 sec, 55° C. for 20 sec, 72° C. for 20 sec. The condition for the asymmetric PCR: 94° C. for 5 min followed by 30 cycles of 94° C. for 20 sec, 52° C. for 20 sec, 72° C. for 20 sec. As shown in Table 1, all the oligonucleotides were purchased from Protect Technology Enterprise Co., Ltd. (Taipei, Taiwan) and used without further purification. The ssDNA probe was perfectly matched to the CC genotype sequence as well as to one-base-pair mismatched to the TT genotype sequence. This two-step PCR simplifies the tedious washing steps by removing the residual reagent and non-specific DNA sequences, promoting the target ssDNA binding onto the microbeads. This allowed the DASH technique to be conducted in the following procedures

TABLE 1

| Name | Sequence | |
|---|---|---|
| Primer-Forward (ATM) | 5'-CTCCCTCTCTACCGCGTCAACGCT-3' | (SEQ. ID NO: 1) |
| Primer-Reverse (ATM) | 5'-CCCAGTAAGAGCATATGTTCAACAT-3' | (SEQ. ID NO: 2) |
| Primer-1-Forward (ATM-A) | 5'-CTTACCCAATACCAGCCGGGCTA-3' | (SEQ. ID NO: 3) |
| Primer-1-Reverse (ATM-A) | 5'-TTTTACCTGAGTCTCGTCTCTCA-3' | (SEQ. ID NO: 4) |
| Primer-2-Forward (ATM-A) | 5'-Biotin-GGCTACGTCCGAGGG-3' | (SEQ. ID NO: 5) |
| Probe-(C-type) | 5'-CCTGCGGCTTGGATCATGCTG-3' | (SEQ. ID NO: 6) |

Names and sequences of the primers and probe used in ATM gene amplification, ATM-A gene amplification and melting curve analysis. The boldface character represents the SNP position of ATM-A.

Verification of Sample's Genotype

In order to verify the genotype of the samples used in the present invention, those samples have been previously genotyped by using commercial real-time PCR machine (MyIQ, Bio-Rad). Briefly, 10 µL of 2× SYBR Green I (Applied Biosystems, Beverly, Mass., USA) and 0.5 µL of probe (10 µM) were added to 10 µL of the product of asymmetric PCR. Once the ssDNA samples were ready, the samples were heated up to 95° C. for 60 seconds for denature the unspecific binding. The melting curve analysis was carried out by cooling temperature down to 55° C. and keeping at this temperature for 60 seconds. The temperature was then gradually increased to 95° C. with 0.1° C./s heating rate; the fluorescent signal was measured for each 0.5° C. interval.

Coupling of Synthetics DNA and PCR DNA to Microbeads

To immobilize the synthetics DNA, the reagent involved mixing of 0.4 µL of 10 µM 5'-biotinylated synthetic DNA, 0.4 µL of 10 µM probe, 10 µL of 2× SYBR Green I, 1 µL of streptavidin-coated microbead suspension (200 beads µL$^{-1}$), and 8.8 µL of ddH$_2$O. The mixture was then incubated at 60° C. for 30 min in a heat block (DB130-1, Firstek Ltd.) to enhance the binding efficiency of streptavidin-coated beads and biotinlayted target-probe duplexes. Meanwhile, to immobilize the DNA sequences from the animal samples, the 10 µL of asymmetric PCR products (ssDNA) and 10 µL of 2× SYBR Green I and 1 µL of 10 µM probe as well as 1 µL of streptavidin-coated microbead suspension (200 beads µL$^{-1}$) were mixing and incubated at 60° C. for 30 min in the heat block.

Data Acquisition on Fluorescent Images

The microfluidic device was placed under an inverted fluorescence microscope (Axio Observer.A1, Carl Zeiss Micro-Imaging GmbH, Göttingen, Germany). The filters for excitation and emission were 425 to 475 nm and 600 to 660 nm according to the spectra of SYBR Green I. The fluorescence signals from the detection mixture were obtained by using a CMOS camera (ORCA-Flash4.0, Hamamatsu, Japan). An exposure time of 50 ms was used in each image acquisition. A background image on liquid flow regions without the beads during the experiment was taken which was automatically subtracted from the later images. The fluorescence intensity of the microchannel was acquired as the background. A series of fluorescence images were captured after one detection mixture (e.g. 10 µL of samples) was examined through the detection region and removed. The positions of the microbead were mapped to a temperature distribution within the channel region and analyzed. Once the detection was completed, DI water was then flushed into the microchannel for cleaning before the next detection mixture was introduced. Detection mixtures of different genotypes (i.e. CC, TT, and CT types) could be then tested in series in a single chip.

Fluorescent Signal Quantification

Relative fluorescence intensity of the target-probe duplex on each 20 µm diameter microbead was quantified based on rom the fluorescent images by using image-processing software, ImageJ (NIH, Bethesda, Mass., USA). The microbeads, which showed higher initial fluorescent intensity and aggregation-free, were chosen as our candidates for DASH technique since they had more target DNA bound on the microbead surface. The fluorescence intensity was then represented by using a normalization function in the following equation:

$$\text{Relative fluorescence intensity} = \frac{X_i - X_{final}}{X_{initial}}$$

where $X_i$ was the fluorescent intensity of a microbead, $X_{final}$ was the final fluorescent intensity of a microbead, and $X_{initial}$ was the initial fluorescent intensity of a microbead. The melting curve profiles are normalized start from 100% and end at 0%. Besides, for statistical significance testing on our results, the p value corresponding to two homogeneous genotypes of ATM-A (CC and TT) was calculated via unpaired Student's t test. Differences with p values less than 0.05 were considered statistically significant.

Results and Discussions

Bead-Based Microfluidic Device

Figure 3:
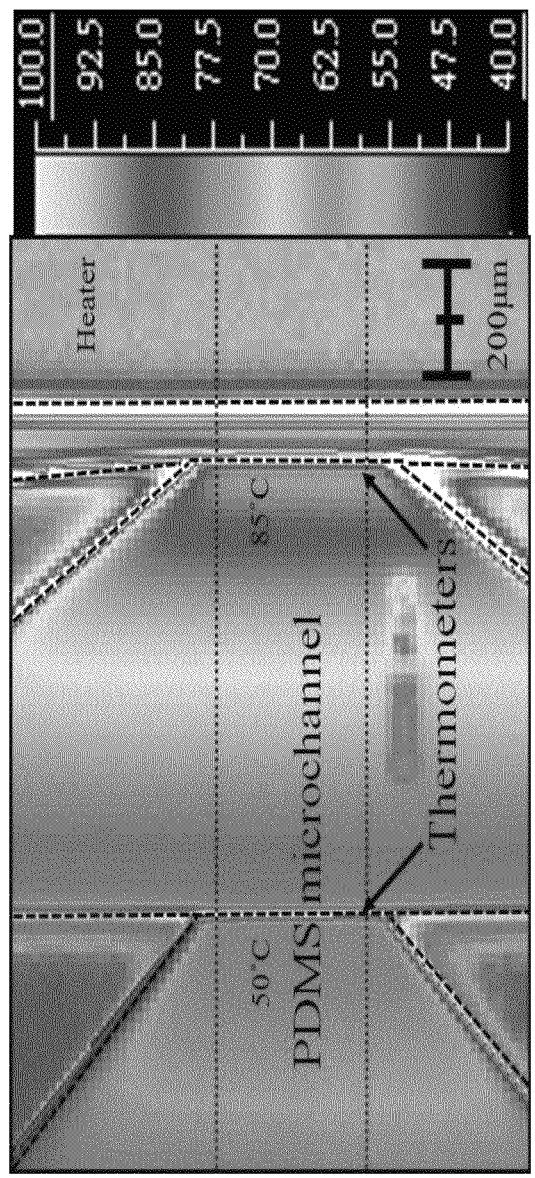
FIG. 3 is an infrared image illustrating the temperature gradient from 50° C. to 85° C. within an 800-µm-long region inside a microchannel.

In the present invention, the microbeads with DNA duplex in a continuous-flow microfluidic device would be detected later in this bead-based microfluidic system. In order to make microbeads with DNA duplex flow smoothly, various combinations of geometric factors (such as the width and height of microchannel) were investigated to improve the efficiency of the microfluidic device. The following combination was adopted in this device: the height and width of the microchannel in 40 µm and 300 µm respectively. The bead-based microfluidic device was tested by injecting plain polystyrene microbeads of 20 µm. Furthermore, the important technical feature of the present invention is to develop a temperature—gradient region by bonding a patterned ITO glass onto the microchannels to make the SNPs detection more efficiency. The heater was mounted on the right side of ITO glass, such that the heat generated from the heater would diffuse from higher temperature region to lower temperature region, thereby forming the temperature gradient region. In addition, a PID control scheme was adopted to create a stable temperature gradient inside a microchannel, as shown in FIG. 3, to in-situ monitor the temperature variation during heating.

SNP Detection Via a Bead-Based Microfluidic Device

Figure 4:
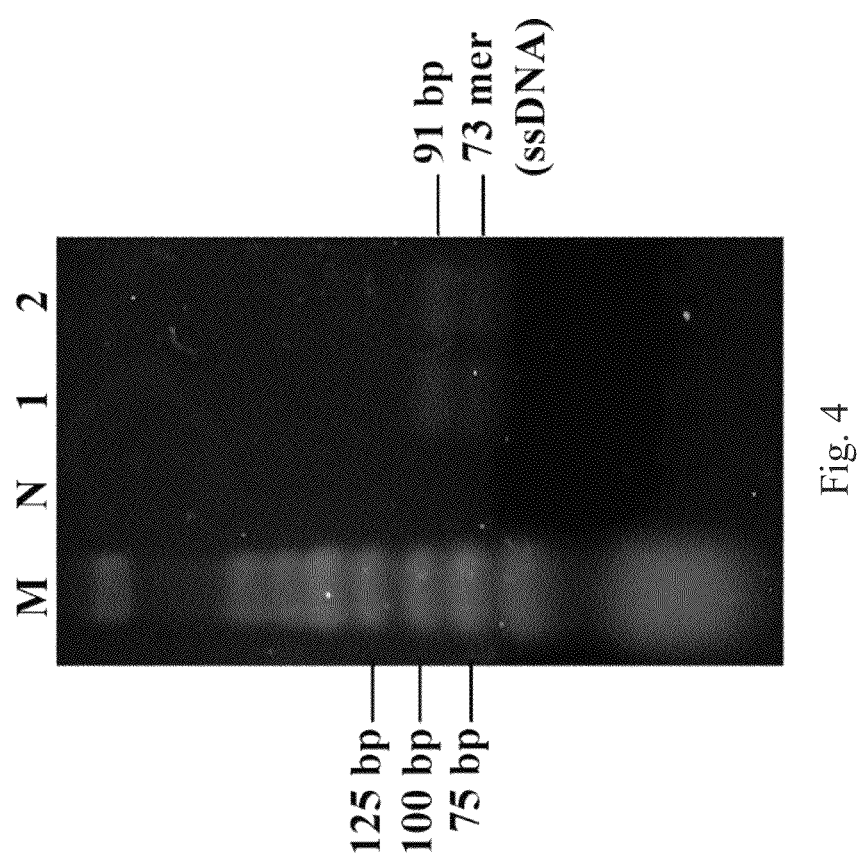
FIG. 4 shows a photograph of an agarose gel electrophoresis of amplified DNA of the ATM-A gene region from two landrace sows run against a negative control: (M) DNA marker; (N) negative control; (1) asymmetric PCR product of wild type (CC genotype); (2) asymmetric PCR product of mutant type (TT genotype)

To confirm the amplified DNA sequence, the PCR products of asymmetric PCR were visualized via electrophoresis on an 2% agarose gel stained with ethidium bromide and compared with the DNA marker (25/100 bp mixed DNA ladder, Bioneer). As shown in FIG. 4, the result brought out that the DNA fragments were 91 bp for as the DNA template and 73 mer for the biotinlayted target ssDNA sequence, as expected. As it revealed the amount of base-pairs in dsDNA, the intercalating dye of ethidium bromide could only exhibit in the self-folding regions for ssDNA, leading to a relatively weaker band. The 73-mer biotinlayted target ssDNA sequence, containing ATM-A SNP point, was also confirmed by the DNA sequencing instrument (Applied Biosystems 3730 DNA Analyzer).

The DNA sequence with a SNP discrimination point ATM-A was chosen and two genotypes (wild and mutant types) were tested. Both the prototype device of the present invention and a commercial machine (Rotor-Gene Q real-time PCR) were utilized for SNP detection. SNP genotyping analysis of each sample was performed using the bead-based microfluidic device by monitoring the fluorescence intensity of the target-probe duplex while the temperature ranged from 50° C. to 85° C. The fluorescence intensity data was then quantified and plotted.

Melting Curve Analysis

Figure 5:
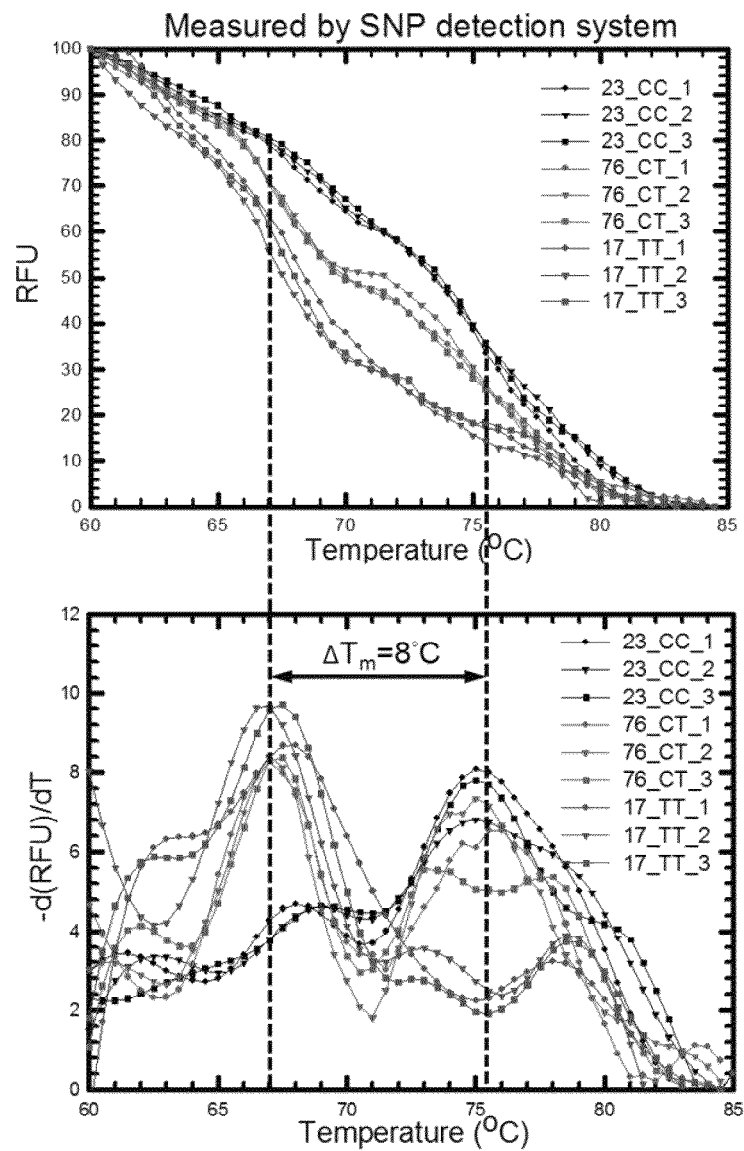
FIG. 5 illustrates melting curves of the three genotypes measured by the SNP detection system of the present invention.

The melting curves for the samples of the three genotypes DNA, including CC, CT, and TT, were acquired, as shown in FIG. 5. At least three microbeads were picked for analysis in each genotype. The genotypes were distinguished by observing the decreasing trend of each curve. The profile of the perfect-match sample (23-CC) had a lower decreasing rate in the beginning (between 60 and 67° C.) due to the larger binding forces between the probe and target ssDNA. The maximum slope change, or the minimum value of the first negative derivatives of the curve, was determined as the melting temperature. The CC genotype sample (23) had the highest melting temperature 75.1° C. and TT genotype sample (17) had the lowest melting temperature 67.1° C. The heterozygous genotype sample (76) showed two melting temperature, 67.2° C. and 75.3° C. Compared to the $T_m$ of homozygous and heterozygous and heterogeneous samples, the difference between the melting temperature ($\Delta T_m$) for CC and TT genotypes was 8° C. Although the melting temperature of the CT genotype (67.2° C. and 75.3° C.) was slight different with the CC (75.1° C.) and TT (67.1° C.) genotype, these errors were less than 0.2° C. and would not affect the results of genotyping.

Figure 6:
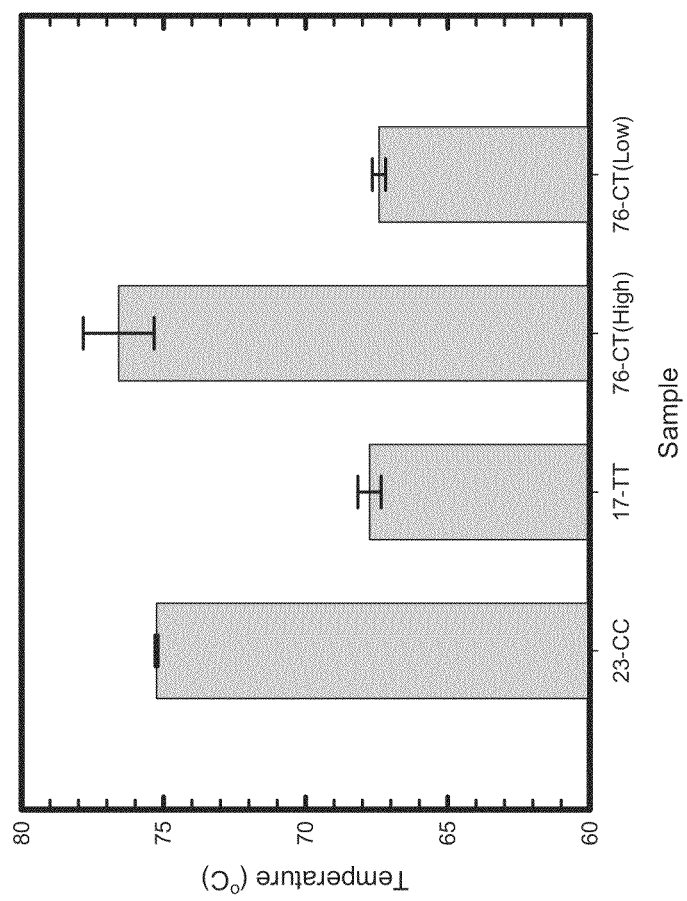
FIG. 6 illustrates melting temperatures of the three genotypes measured by the SNPs detection system of the present invention.

The melting temperatures of the three genotypes were summarized in FIG. 6. All of the melting temperatures were determined by finding the negative maximum of their first derivatives. The p value of the two peaks was $7.9 \times 10^{-6}$, proving that the three genotypes could be statistically distinguished.

Melting Curve Analysis by Rotor-Gene Q System

Figure 7:
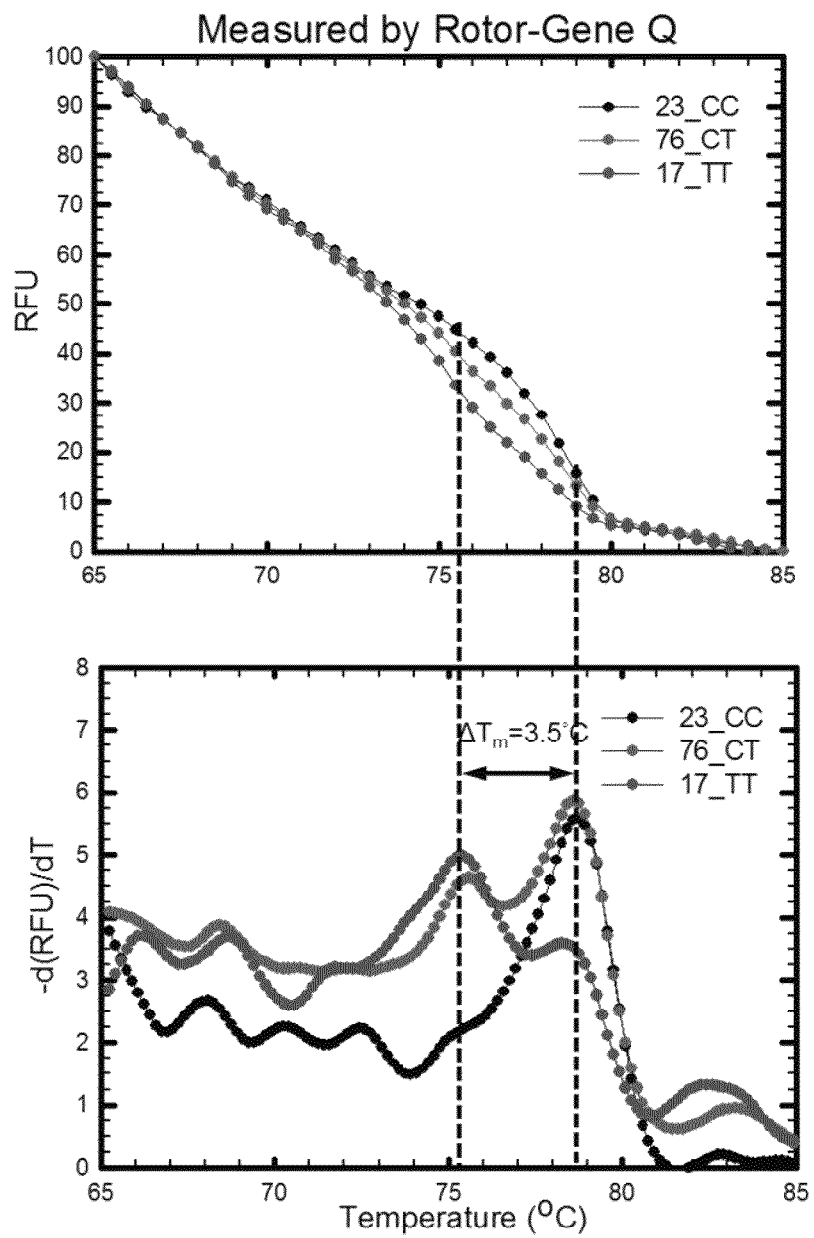
FIG. 7 illustrates melting curve of the three genotypes measured by Rotor-Gene Q machine.

The other approach of melting analysis was conducted by using Rotor-Gene Q system, and its results were as shown in FIG. 7. The process parameters for this melting analysis were also listed in Table 2.

The CC genotype sample (23) had the melting temperature 78.8° C. and TT genotype sample (17) had the melting temperature 75.3° C. The heterozygous genotype sample (76) showed two melting temperature, 75.5° C. and 78.6° C. Compared to the $T_m$ of homozygous and heterozygous samples, the $\Delta T_m$ was 3.5° C. The three genome types were successfully genotyping via melting curve analysis by commercial tool (Rotor-Gene Q system).

TABLE 2

| The melting curve detection recipe of the Rotor-Gene Q | |
|---|---|
| Step | Parameter |
| Pre-heating temperature | 95° C. |
| Pre-heating time | 5 mins |
| Detection region (temperature) | 65° C.~85° C. |
| Heating rate | 0.1° C./second |

Comparisons of the Bead-Based SNP Detection System and Rotor-Gene Q System

The spatial resolution of the melting curve measured by our SNP detection system is determined by the sCMOS detector array, the optic detection path, and the temperature gradient distribution. The pixel resolution of the sCMOS detector in these experiments was 1638 pixels/mm, resulting in temperature of 0.00000122° C./pixel. On the other words, the maximum temperature difference on the 20 μm microbeads surface was about 0.4° C.

The results of the genotyping by our system (bead-based microfluidic, spatial melting analysis) and Rotor-Gene Q system (tube-based, temporal melting analysis) were consistent. The $\Delta T_m$ of 8° C. by our bead-based microfluidic device was about 2.5 times larger than the $\Delta T_m$ of 3.5° C. by Rotor-Gene Q system. Larger $\Delta T_m$ would be beneficial to distinguish the perfect match duplex and the mismatch duplex. Reason for this advantage could be due to the excellent heating rate.

Table 3 made the comparisons between our bead-based SNP detection system and tube-based Rotor-Gene Q system. In the bead-based device, the embedded temperature control unit in the microchannel not only provided the precise temperature control but also the large temperature variation within a small distance, because of better heat transfer at microscale from scaling, resulting in a rapid heating rate on the microbeads. The heating rate of our SNP detection system was determined by the microbead flow rate and the temperature in the microchannel, this system was estimated to have about 0.62° C./second average heating rate, compared to 0.1° C./second from the tube-based system. In addition, because the temperature field was generated in the microchannel before the mixture was introduced to the detection region, the heating rate would be affected by the flow rate of the mixture. It was recommended to have the same flow rate on the tests for one SNP location to ensure similar flow dynamics and heat conduction for the microbeads and microchannels.

Furthermore, although the volumes for the detection mixture in both approaches were similar, the bead-based system could use as few as three microbeads (or even one microbead) for melting curve analysis. In other words, the bead-based approach of the present invention was estimated to require as few as $10^5$ strings of ssDNA for detection, far less than $10^{12}$ strings of ssDNA, which were needed by the tube-based system. Additionally, the detection time for each genotype only took less than 30 minutes when the bead-based device was used, compared to 45 minutes when Rotor-Gene Q was used. Moreover, among 30 minutes in the total detection time took, 15 minutes were needed on the mixture injection procedure.

Also, to improve the detection efficiency and reduce the detection time, the mixture injection procedure could be assisted by using automation loading system, which was consisted with switch valve, two more syringe pump, syringe, and computer to conduct the mixture injection procedure.

TABLE 3

Comparisons of the NTU bead-based SNP detection system and Rotor-Gene Q system

| Detection system | NTU | Rotor-Gene Q |
|---|---|---|
| Detection environment | Microfluidics | Tube |
| Detection principle | Melting curve | Melting curve |
| Heating rate | 0.62° C./sec | 0.1° C./sec |
| $\Delta T_m$ | 8° C. | 3.5° C. |
| Detection sample required | 10 μL @ 10 mM | 22 μL @ 10 mM |
| DNA amount (string) used for detection | <$10^5$ | ≈$10^{12}$ |
| Detection time | <30 minutes | 45 minutes |

To sum up, a novel SNP genotyping system of the present invention is developed by conducting DASH technique on microbeads in microfluidic devices. The DNA duplexes were conjugated onto silica microbeads and the melting curve analysis was performed in the temperature gradient region. Also, SNP detection on single microbead was achieved in a very short time. The genotyping results of ATM-A mutation were compared to the results obtained from commercial genotyping instrument, verifying the reliability of the developed system. Finally, the present invention can be further integrated with PCR capability to simplify the DNA amplification and isolation procedures. The volume reduction and rapid analysis that the present invention can provide the potential of being a cost-effective and high-throughput SNP detection method in genotyping applications.

In accordance with the present invention, the method of SNP detection by using DASH technique in bead-based microfluidics has the following advantages:

(1) The temperature gradient region is designed in the present invention. When the microbeads with DNA duplex flow through this region, the flow rate are increased and the temperature of microbeads as well as DNA duplex can increase immediately, so as to enhance measurement sensitivity.

(2) Compared with conventional DASH technique, samples of the present invention can be assembled by the microbeads (solid support), such that not merely can the background interference be reduced but the sensitivity and the detection limit can also be increased.

(3) The microbeads not only provide a relatively higher surface-to-volume ratio for biomolecule immobilization, but also have the advantages of enhancing reaction kinetics and reducing background noise. The microbeads has excellent ability for heat transfer to make the heat exchange promptly between the microbeads and environment during heating, so as to ensure that the reaction temperature for DNA duplex on microbeads is the same as the environment temperature and improve the measurement accuracy.

It will be understood that the above description of embodiments is given by way of example only and that various modifications may be made by those with ordinary skill in the art. The above specification, examples, and data provide a complete description of the present invention and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of single nucleotide polymorphism (SNP) detection by using gene detection technique in bead-based microfluidics comprising following steps:
   (a) preparing a microbead with a duplex DNA;
   (b) inserting a dye into the duplex DNA;
   (c) delivering the microbead into a microchannel with a temperature gradient region;
   (d) heating the temperature gradient region to denature the duplex DNA;
   (e) monitoring a fluorescence intensity of the duplex DNA during the step (d) to obtain a melting curve; and
   (f) determining the SNP by a melting curve analysis method;
   wherein the duplex DNA is synthesized by a target single-strand DNA and an allele-specific probe.

2. The method of claim 1, wherein the target single-strand DNA is amplified by PCR.

3. The method of claim 2, wherein after the target single-strand DNA is amplified by PCR, the target single-strand DNA is biotinlayted and the microbead is coated with streptavidin.

4. The method of claim 3, wherein the target single-strand DNA is immobilized onto the microbead by a biotin-streptavidin interaction.

5. The method of claim 4, wherein after the target single-strand DNA is immobilized onto the microbead, the allele-specific probe is hybridized with the target single-strand DNA.

6. The method of claim 1, wherein a patterned glass configured with a thermometer and a heater are bonded onto the microchannel.

7. The method of claim 6, wherein a temperature of the temperature gradient region is controlled by a heater.

8. The method of claim 6, wherein a temperature of the temperature gradient region is detected by the thermometer.

9. The method of claim 1, wherein the fluorescence intensity is monitored by a CCD camera.

10. The method of claim 1, wherein the dye is an intercalating dye.

11. The method of claim 10, wherein the intercalating dye comprises SYBR Green I, EtBr or EVA Green.

12. The method of claim 1, wherein the temperature gradient region is heated ranged from 50° C. to 95° C.

* * * * *

SEQUENCE LISTING

```
<160> NUMBER OF SEQ ID NOS: 6

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
ctccctctct accgcgtcaa cgct                                        24

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
cccagtaaga gcatatgttc aacat                                       25

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
cttacccaat accagccggg cta                                         23
```

```
<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ttttacctga gtctcgtctc tca                                              23

<210> SEQ ID NO 5
<211> LENGTH: 15
<212> TYPE: DNA
<213> ORGANISM: Artificial Sequence
<220> FEATURE:
<223> OTHER INFORMATION: Primer

<400> SEQUENCE: 5
ggctacgtcc gaggg                                                       15

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
cctgcggctt ggatcatgct g                                                21
```